US009599578B2

(12) United States Patent
Yanagita et al.

(10) Patent No.: US 9,599,578 B2
(45) Date of Patent: Mar. 21, 2017

(54) CONTROL METHOD OF RADIATION TOMOGRAPHIC IMAGING APPARATUS, RADIATION TOMOGRAPHIC IMAGING APPARATUS AND PROGRAM

(71) Applicant: General Electric Company, Schenectady, NY (US)

(72) Inventors: Hirofumi Yanagita, Tokyo (JP); Ryosuke Fujimoto, Tokyo (JP)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 345 days.

(21) Appl. No.: 14/494,119

(22) Filed: Sep. 23, 2014

(65) Prior Publication Data

US 2015/0092908 A1 Apr. 2, 2015

(30) Foreign Application Priority Data

Sep. 27, 2013 (JP) .................. 2013-201307

(51) Int. Cl.
| | |
|---|---|
| A61B 6/00 | (2006.01) |
| H05G 1/54 | (2006.01) |
| G01N 23/04 | (2006.01) |
| A61B 6/03 | (2006.01) |
| F16C 17/10 | (2006.01) |
| H05G 1/56 | (2006.01) |

(52) U.S. Cl.
CPC ........... *G01N 23/046* (2013.01); *A61B 6/035* (2013.01); *F16C 17/107* (2013.01); *H05G 1/54* (2013.01);
(Continued)

(58) Field of Classification Search
CPC ........... A61B 6/03; A61B 6/032; A61B 6/035; A61B 6/10; A61B 6/102; A61B 6/105;
(Continued)

(56) References Cited

U.S. PATENT DOCUMENTS 5,212,437 A * 5/1993 Hescht .................. A61B 6/032
318/778
5,696,804 A * 12/1997 Ono ....................... A61B 6/032
378/125
(Continued)

FOREIGN PATENT DOCUMENTS

| CN | 101944470 A | 1/2011 |
| CN | 102415219 A | 4/2012 |

(Continued)

OTHER PUBLICATIONS

First CN office action, including English translation, for corresponding CN application No. 201410501166.1 dated Jul. 6, 2016; 11 pages.

*Primary Examiner* — Thomas R Artman
(74) *Attorney, Agent, or Firm* — Fletcher Yoder, P.C.

(57) ABSTRACT

A control method of a radiation tomographic imaging apparatus having a gantry rotating section equipped with a radiation tube including a liquid bearing and a rotor configured to support an anode and configured to rotate is provided. The control method includes a control step that is configured to start a rotation of the gantry rotating section at a second velocity slower than a first velocity, start control for stopping the rotation of the rotor, and control the gantry rotating section and the radiation tube so as to stop the gantry rotating section at a home position. The control method further includes a setting step configured to set at least one of the second velocity and the delay time such that a rotational angular position of the gantry rotating section at a time that the rotor stops rotation averagely varies when a shutdown is performed plural times.

20 Claims, 5 Drawing Sheets

(52) U.S. Cl.
CPC ........ *H05G 1/56* (2013.01); *H01J 2235/1086* (2013.01)

(58) Field of Classification Search
CPC ... A61B 6/54; A61B 6/56; H05G 1/02; H05G 1/025; H05G 1/08; H05G 1/10; H05G 1/26; H05G 1/30; H05G 1/54; H05G 1/56; H01J 35/02; H01J 35/10; H01J 35/101; H01J 35/105; H01J 35/106; H01J 35/26; H01J 35/305; H01J 2235/10; H01J 2235/1046; H01J 2235/106; H01J 2235/12; H01J 2235/1216; H01J 2235/1225; H01J 2235/1258
See application file for complete search history.

(56) References Cited

U.S. PATENT DOCUMENTS

| | | | |
|---|---|---|---|
| 6,276,145 B1 | 8/2001 | Sharpless et al. | |
| 6,322,248 B1 | 11/2001 | Yanagita et al. | |
| 6,449,337 B1 * | 9/2002 | Honda | H05G 1/54 378/117 |
| 6,937,697 B2 | 8/2005 | Nishide et al. | |
| 8,433,031 B2 | 4/2013 | Nukui et al. | |
| 2011/0002564 A1 | 1/2011 | Essensohn et al. | |
| 2012/0039442 A1 * | 2/2012 | Saito | H01J 35/26 378/112 |
| 2012/0220852 A1 | 8/2012 | Bentham et al. | |
| 2013/0243161 A1 * | 9/2013 | Hishikawa | H01J 35/10 378/93 |

FOREIGN PATENT DOCUMENTS

| | | |
|---|---|---|
| CN | 102665567 A | 9/2012 |
| EP | 1095620 A1 | 5/2001 |
| JP | 8112274 A | 5/1996 |
| JP | H08212949 A | 8/1996 |
| JP | 2001276034 A | 10/2001 |
| JP | 2002272728 A | 9/2002 |
| JP | 4678964 B2 | 4/2011 |

\* cited by examiner

CONTROL METHOD OF RADIATION TOMOGRAPHIC IMAGING APPARATUS, RADIATION TOMOGRAPHIC IMAGING APPARATUS AND PROGRAM

CROSS REFERENCE TO RELATED APPLICATIONS

This application claims the benefit of Japanese Patent Application No. 2013-201307 filed Sep. 27, 2013, which is hereby incorporated by reference in its entirety.

BACKGROUND

The present invention relates to a technology for controlling a radiation tomographic imaging apparatus equipped with a radiation tube having a liquid bearing.

As a radiation tube installed in a gantry rotating section of a radiation tomographic imaging apparatus, there has been proposed a radiation tube based on a liquid bearing, i.e., a liquid bearing system (refer to Japanese Unexamined Patent Publication No. Hei 08 (1996)-212949 and the like). In the radiation tube of the liquid bearing system, a liquid metal lubricant has been used in a bearing of a rotor that supports an anode. In this type of radiation tube, as compared with a conventional ball bearing system, mechanical friction is remarkably reduced and the conductivity of heat from the anode to the bearing is improved, thereby making it possible to realize a long lifetime, miniaturization and a large heat capacity.

Meanwhile, generally, the rotation of the rotor of the radiation tube is started when the radiation tomographic imaging apparatus is started up, and is stopped when the radiation tomographic imaging apparatus is shut down. As shown in FIG. 5, in a liquid bearing type radiation tube, when a rotor is stopped, the anode side of the rotor is slightly lowered by its own weight and the side opposite to the anode of the rotor is slightly elevated. At this time, the inner edge portion of the rotor on the side opposite to the anode thereof is brought into contact with the surface of a bearing. Thus, the inner edge on the side opposite to the anode of the rotor makes contact with the surface of the bearing on its gravity direction side while rotating at the moment when the rotating rotor is completely stopped, so that its contact portion is slightly damaged. The bearing is normally fixed to a housing for the radiation tube. Therefore, if a rotational angular position of a gantry rotating section at the time of the stop of the rotor is always the same, the portion of the bearing on its gravity direction side, i.e., damaged portion becomes always the same, thus resulting in shortening of the life of the bearing.

Incidentally, there has been disclosed in Japanese Patent No. 4678964, a method of changing on every occasion, a rotational angular position where a gantry rotating section is stopped, when a radiation tomographic imaging apparatus is shut down.

On the other hand, when the radiation tomographic imaging apparatus is shut down, the gantry rotating section is desirably stopped at a rotational angular position, a so-called home position to stop it when no scan is done, because of various reasons.

For example, the radiation tomographic imaging apparatus is often generally configured such that when the gantry rotating section is being stopped at the home position, a positioning light installed in the gantry rotating section is placed in a proper position to perform alignment of a subject. In this case, when the radiation tomographic imaging apparatus is shut down, the gantry rotating section is desirably stopped at the home position in such a manner that the subject alignment can be performed even immediately after the radiation tomographic imaging apparatus is restarted up.

Also, for example, the radiation tomographic imaging apparatus can be configured in such a manner that when the gantry rotating section is being stopped at the home position, the radiation tube and its heat exhausting unit provided to a gantry housing section most approach each other and the heat exhaust of the radiation tube is efficiently performed. The heat exhaust of the radiation tube is performed to suppress damage due to the heat storage of the radiation tube and shorten a waiting time till the radiation tube is cooled quickly to enable scanning. In such a case, it is desirable to stop the gantry rotating section at the home position in such a manner that the heat exhaust of the radiation tube is effectively performed when the scan is not done. Further, when the radiation tomographic imaging apparatus is shut down, the gantry rotating section is desirably stopped at the home position such that the heat exhaust of the radiation tube is started quickly when the radiation tomographic imaging apparatus is restarted up.

Further, for example, the radiation tomographic imaging apparatus can be configured in such a manner that when the gantry rotating section is stopped at the home position, a detector and its heat retaining unit provided to the gantry housing section most approach each other and the heat retention of the detector is performed efficiently. The heat retention of the detector is mainly performed to stabilize the detection property of the detector and stabilize the quality of a reconstructed image. In such a case, when the scan is not performed, the gantry rotating section is desirably stopped at the home position such that the heat retention of the radiation tube is effectively performed. Further, when the radiation tomographic imaging apparatus is shut down, the gantry rotating section is desirably stopped at the home position such that the heat retention of the radiation tube is started quickly when the radiation tomographic imaging apparatus is restarted up.

The following radiation tomographic imaging apparatus can be imagined regarding a temporary stop position and the home position. When the radiation tomographic imaging apparatus is shut down, the operation of rotating the gantry rotating section to the set rotational angular position and temporarily stop the gantry rotating section, and thereafter rotating the gantry rotating section again after a while and returning the same to the home position is performed.

With this situation in view, there has been a demand for a technology capable of shutting down a radiation tomographic imaging apparatus equipped with a radiation tube having a liquid bearing without shortening the life of the radiation tube and in safety.

BRIEF DESCRIPTION

In a first aspect, a control method of a radiation tomographic imaging apparatus having a gantry rotating section equipped with a radiation tube including a rotor supporting an anode and rotating and a liquid bearing, and a detector is provided. The control method includes a control step for when the radiation tomographic imaging apparatus is shut down, starting the rotation of the gantry rotating section at a second velocity slower than a first velocity being a velocity at an actual scan thereof, starting control for stopping the rotation of the rotor after a predetermined delay time has elapsed from the starting point of the rotation, and controlling the gantry rotating section and the radiation tube so as to stop the gantry rotating section at a home position after the rotation of the rotor is stopped, and a setting step for setting the second velocity and/or the delay time in such a manner that a rotational angular position of the gantry rotating section at the time of the stop of the rotor rotation averagely varies when the shutdown is performed plural times.

In a second aspect, the control method according to the first aspect is provided, wherein in the setting step, the delay time is set at random.

In a third aspect, the control method according to the first aspect is provided, wherein in the setting step, any of a plurality of delay times different from each other is sequentially set in accordance with a prescribed pattern.

In a fourth aspect, the control method according to any one of the first to third aspects is provided, wherein the second velocity is a velocity that takes 10 seconds or more per rotation.

In a fifth aspect, the control method according to any one of the first to fourth aspects is provided, wherein the home position is a rotational angular position in which the irradiation direction of a positioning light installed in the gantry rotating section becomes a specific direction.

In a sixth aspect, the control method according to any one of the first to fifth aspects is provided, wherein the home position is a rotational angular position at which the radiation tube approaches a heat exhausting unit therefor.

In a seventh aspect, the control method according to any one of the first to sixth aspects is provided, wherein the home position is a rotational angular position at which the detector approaches a heat retaining unit therefor.

In an eighth aspect, a radiation tomographic imaging apparatus having a gantry rotating section equipped with a radiation tube including a rotor supporting an anode and rotating and a liquid bearing, and a detector is provided. The apparatus includes a control unit for when the radiation tomographic imaging apparatus is shut down, starting the rotation of the gantry rotating section at a second velocity slower than a first velocity being a velocity at an actual scan thereof, starting control for stopping the rotation of the rotor after a predetermined delay time has elapsed from the starting point of the rotation, and controlling the gantry rotating section and the radiation tube so as to stop the gantry rotating section at a home position after the rotation of the rotor is stopped, and a setting unit for setting the second velocity and/or the delay time in such a manner that a rotational angular position of the gantry rotating section at the time of the stop of the rotor rotation averagely varies when the shutdown is performed plural times.

In a ninth aspect, the radiation tomographic imaging apparatus according to the eighth aspect is provided, wherein the setting unit sets the delay time at random.

In a tenth aspect, the radiation tomographic imaging apparatus according to the eighth aspect is provided, wherein the setting unit sequentially sets any of a plurality of delay times different from each other in accordance with a prescribed pattern.

In an eleventh aspect, the radiation tomographic imaging apparatus according to any one of the eighth to tenth aspects is provided, wherein the second velocity is a velocity that takes 10 seconds or more per rotation.

In a twelfth aspect the radiation tomographic imaging apparatus according to any one of the eighth to eleventh aspects, wherein the home position is a rotational angular position in which the irradiation direction of a positioning light installed in the gantry rotating section becomes a specific direction.

In a thirteenth aspect, the radiation tomographic imaging apparatus according to any one of the eighth to twelfth aspects is provided, wherein the home position is a rotational angular position at which the radiation tube approaches a heat exhausting unit therefor.

In a fourteenth aspect, the radiation tomographic imaging apparatus according to any one of the eighth to thirteenth aspects is provided, wherein the home position is a rotational angular position at which the detector approaches a heat retaining unit therefor.

In a fifteenth aspect, a program for functioning a computer as the control unit and the setting unit in the radiation tomographic imaging apparatus according to any one of the aspects 8 to 14 is provided.

According to the above aspects, a radiation tomographic imaging apparatus equipped with a radiation tube having a liquid bearing can be shut down without shortening the life of the radiation tube and in safety.

Further advantages will be apparent from the following description of the exemplary embodiments as illustrated in the accompanying drawings.

DETAILED DESCRIPTION

An exemplary embodiment will be described below. Incidentally, the disclosure is not limited thereby.

Figure 1:
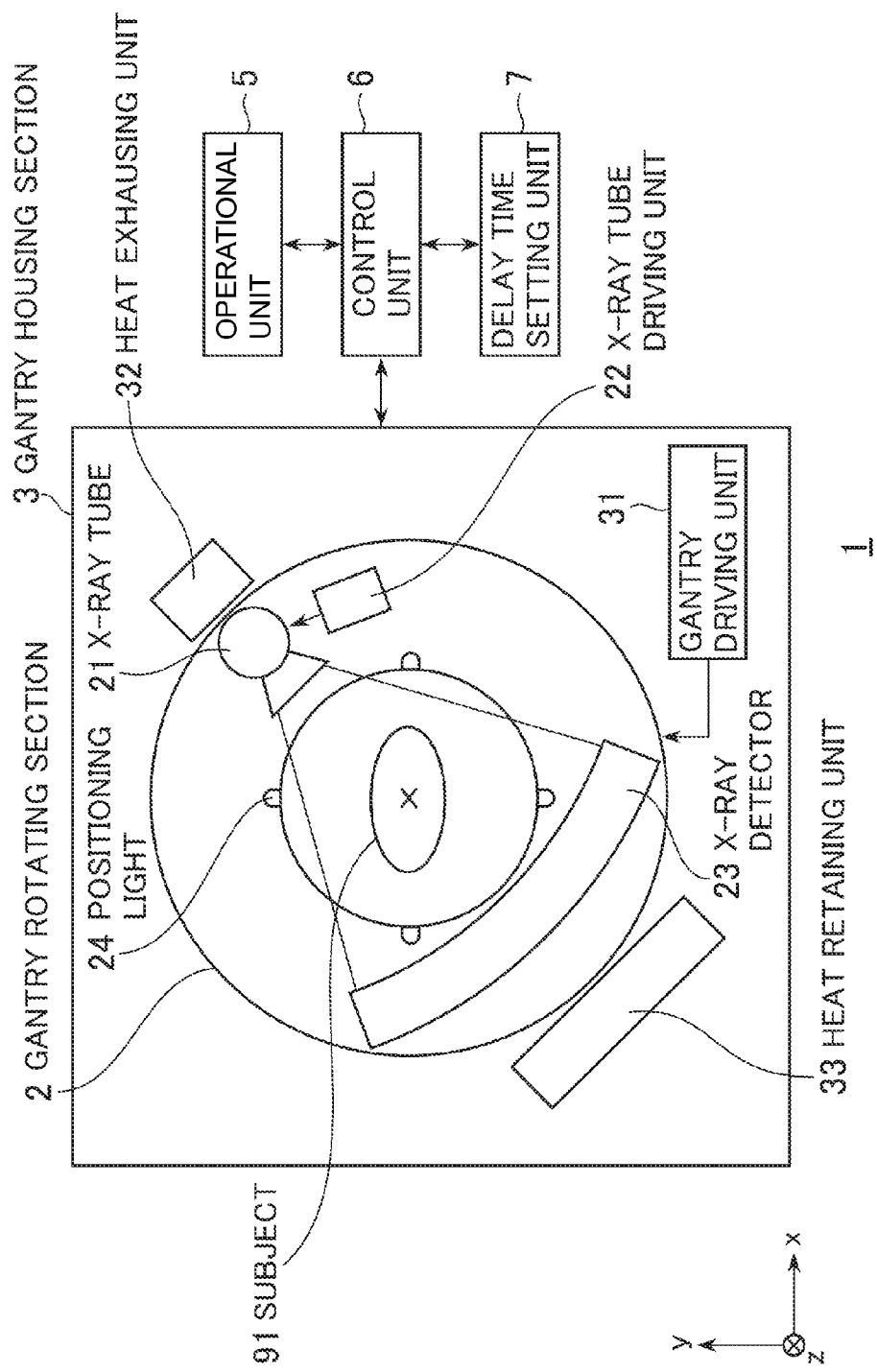
FIG. 1 is a diagram schematically showing a configuration of a part related to drive control in an X-ray CT apparatus according to the exemplary embodiment.

FIG. 1 is a diagram schematically showing a configuration of a part related to drive control of an X-ray CT (Computed Tomography) apparatus 1 according to the exemplary embodiment. As shown in FIG. 1, the X-ray CT apparatus 1 has a gantry rotating section 12 and a gantry housing section 3.

The gantry rotating section 2 is supported by the gantry housing section 3 so as to be rotatable with a virtual axis extending in a z-direction as a rotation axis. The gantry rotating section 2 rotates when performing the scan and stops at a home position HP when not performing the scan. The rotational velocity of the gantry rotating section 2 at its scan execution is a velocity of about 0.25 to 1 seconds per rotation, for example. The home position HP takes a rotational angular position of 45° when the rotational angular position at the time that an X-ray tube 21 is placed in the highest position is 0°, for example.

The gantry rotating section 2 is equipped with the X-ray tube 21, an X-ray tube driving unit 22, an X-ray detector 23 and a positioning light 24.

The X-ray tube 21 radiates X-rays to a subject.

Figure 2:
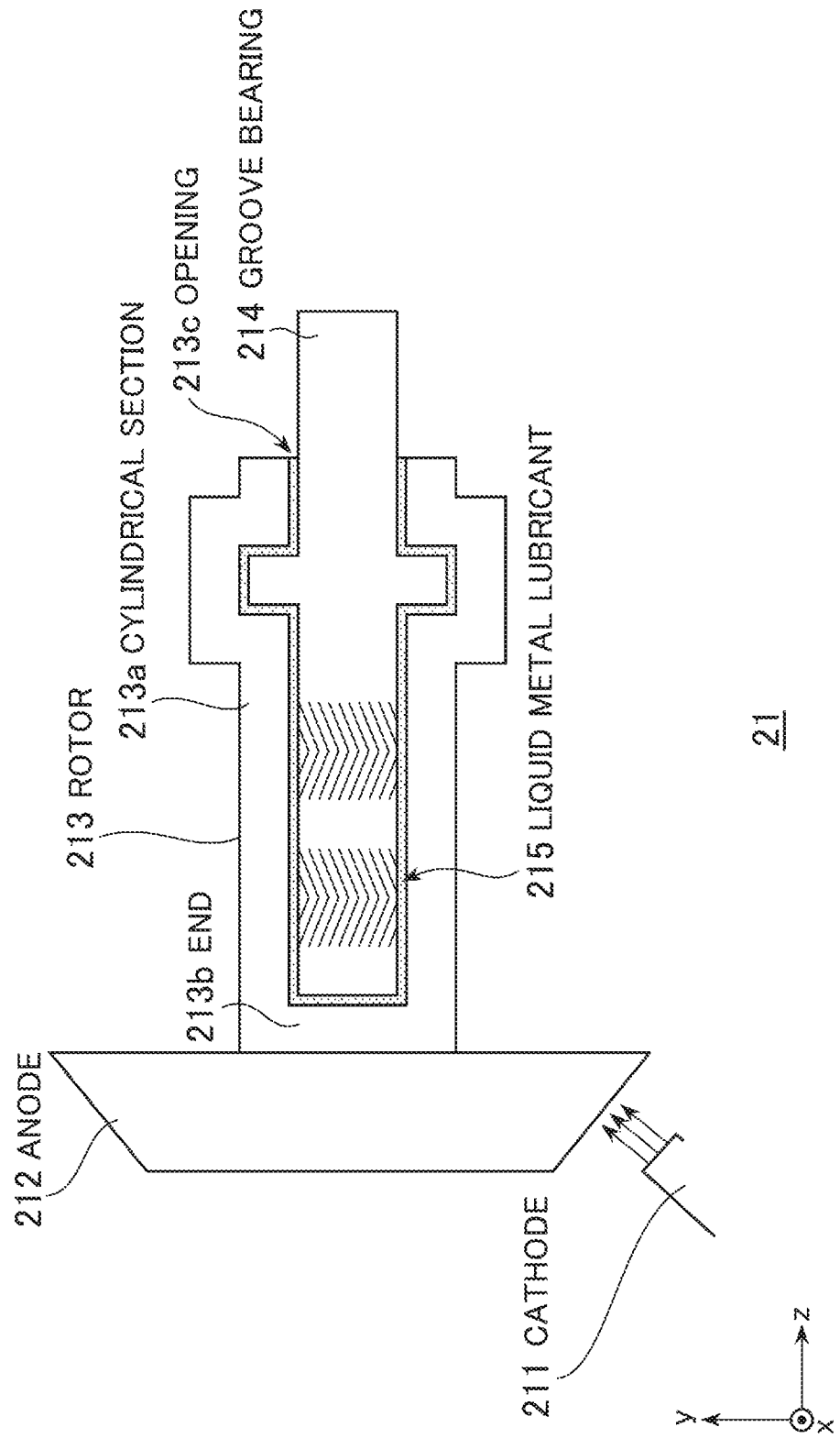
FIG. 2 is a diagram illustrating a configuration of an X-ray tube.

FIG. 2 is a diagram showing the configuration of the X-ray tube 21. As shown in FIG. 2, the X-ray tube 21 has a cathode 211, an anode 212, a rotor 213, a groove bearing 214, and a liquid metal lubricant 215.

The rotor 213 has a cylindrical section 213a and an end 213b which closes one opening of the cylindrical section 213a. The anode 212 has a disk shape, and the end 213b of the rotor 213 is fixed to the center of the anode 212. The groove bearing 214 is inserted into the cylindrical section 213a of the rotor 213. A slight gap is formed between the cylindrical section 213a of the rotor 213 and the groove bearing 214. The liquid metal lubricant 215 is filled in the gap. The other opening of the cylindrical section 213a of the rotor 213 is shielded so as to avoid leakage of the liquid metal lubricant 215 therefrom. The rotor 213 and the groove bearing 214 are configured to prevent the rotor 213 from being detached from the groove bearing 214. The rotor 213 rotates about the groove bearing 214. The anode 212 is rotated by rotating the rotor 213. Electrons are emitted from the cathode 211 and caused to collide with the rotating anode 211 to thereby generate X-rays. Incidentally, the gap has a thickness of several tens of microns (μm) or so. Further, the liquid metal lubricant 215 is composed of, for example, a gallium alloy.

The X-ray driving unit 22 rotationally drives the rotor 213 of the X-ray tube 21, based on a control signal received thereat. For example, the X-ray driving unit 22 accelerates the rotor 213 of the X-ray tube 21 from its stop state to perform a constant-velocity rotation thereof or decelerates the rotor 213 from the state of its constant-velocity rotation to stop the rotor 213.

The X-ray detector 23 detects X-rays that transmits the subject. The X-ray detector 23 is comprised of a plurality of detecting elements arranged in a matrix form.

When the gantry rotating section 2 is placed in the home position HP, the positioning light 24 irradiates the subject with a light beam in horizontal and vertical directions. An operator performs alignment of the subject before scanning on the basis of the light beam applied to the subject.

The gantry housing section 3 is provided with a gantry driving unit 31, a heat exhausting unit 32 and a heat retaining unit 33.

The gantry driving unit 31 rotationally drives the gantry rotating section 2, based on a control signal received thereat. For example, the gantry driving unit 31 constant-velocity rotates the gantry rotating section 2 at a high velocity Vg1 when performing the scan and stops it at a rotational angular position set as the home position HP when not performing the scan. Further, when the X-ray CT apparatus is shut down, for example, the gantry driving unit 31 constant-velocity rotates the gantry rotating section 2 at a low velocity Vg2, or stops it at the rotational angular position set as the home position HP.

When the gantry rotating section 2 is placed in the home position HP, the heat exhausting unit 32 most approaches the X-ray tube 21 and is arranged in a position opposite to the X-ray tube 21. The heat exhausting unit 32 is made up of an intake fan, an exhaust duct, etc. When the gantry rotating section 2 is being stopped at the home position HP, the heat exhausting unit 32 sucks heated air from around the X-ray tube 21 and exhausts it to the outside of the gantry housing section 3. It is thus possible to efficiently cool the X-ray tube 21, suppress damage to the X-ray tube 21 due to its heat storage and shorten a scan standby time required to cool the X-ray tube 21. Incidentally, unless a main power supply of the X-ray CT apparatus 1 is turned off, the heat exhausting unit 32 is always being operated even if the X-ray CT apparatus 1 is shut down.

When the gantry rotating section 2 is placed in the home position HP, the heat retaining unit 33 most approaches the X-ray detector 23 and is arranged in a position opposite to the X-ray detector 23. The heat retaining unit 33 is comprised of a heater, a blower, etc. When the gantry rotating section 2 is being stopped at the home position HP, the heat retaining unit 33 applies hot air to the X-ray detector 23 to hold the X-ray detector 23 at a constant temperature. It is thus possible to efficiently keep the X-ray detector 23 warm and suppress fluctuations in the quality of an image obtained by imaging. Incidentally, unless the main power supply of the X-ray CT apparatus 1 is shut down, the heat retaining unit 33 is always being operated even if the X-ray CT apparatus 1 is shut down.

The X-ray CT apparatus 1 further has an operation unit 5, a control unit 6 and a delay time setting unit 7.

The operation unit 5 receives various operations from the operator.

In response to the startup operation of the X-ray CT apparatus 1 by the operator, the control unit 6 performs control of the respective parts including the gantry driving unit 31, the X-ray tube driving unit 22, etc. to start up the X-ray CT apparatus 1. The control unit 6 performs the following control, for example. First, the rotation of the gantry rotating section 2 is started. The rotational velocity at this time is a velocity that takes about 1 to 3 seconds per rotation, for example. In the present example, the rotational velocity is assumed to be a velocity that takes 2 seconds per rotation. When the gantry rotating section 2 is shifted to the constant-velocity rotation, the rotation of the rotor 213 of the X-ray tube 21 is started when the rotational angular position of the gantry rotating section 2 ranges from −45° to +45°. When the gantry rotating section 2 is rotated at the above rotational velocity and the rotational angular position is within this range, the gravity and centrifugal force applied to the rotor 213 are balanced so that the rotor 213 and the groove bearing 214 are brought into a non-contact state. If the rotation of the rotor 213 is started at this time, the groove bearing 214 is not damaged. When the rotor 213 is shifted to the constant-velocity rotation, the gantry rotating section 2 is stopped at the home position HP in a state in which the rotation of the rotor 213 is maintained.

Also, the control unit 6 performs control of the respective parts including the gantry driving unit 31, the X-ray tube driving unit 22, etc. in such a manner that a scan is executed in accordance with a set scan condition.

Further, in response to the operation of shutdown of the X-ray CT apparatus 1 by the operator, the control unit 6 performs control of the respective parts including the gantry driving unit 31, the X-ray tube driving unit 22, etc. to shut down the X-ray CT apparatus 1. The control unit 6 performs the following control, for example. First, the rotation of the gantry rotating section 2 is started. The rotational velocity at this time is a second velocity slower than a first velocity that is a velocity at an actual scan, e.g., a velocity that takes 10 seconds or more per rotation. In the present example, the second velocity is assumed to be a velocity that takes 20 seconds per rotation. After a predetermined delay time set by the delay time setting unit 7 has elapsed since the start point of the rotation, control on the stop of rotation of the rotor 213 is started. After the stop of the rotation of the rotor 213, the gantry rotating section 2 is stopped at the home position.

The delay time setting unit 7 sets the above delay time. The delay time is set in such a manner that when the shutdown is performed plural times, the rotational angular position of the gantry rotating section at the stop of the rotation of the rotor varies averagely. In the present example, a delay time within 20 seconds that are a time necessary for the gantry rotating section 2 to rotate one time is set at random using a random number or the like. Incidentally, the delay time setting unit 7 may select and set any of a plurality of delay times determined in advance and different from each other sometimes or every time in accordance with a prescribed pattern (according to the prescribed order, for example). Further, the delay time may be determined based on other factors such as the imaging date and time, the number of counts of shutdown, etc. Furthermore, the delay time may be set to zero.

Incidentally, the control unit 6 and the delay time setting unit 7 can be achieved by allowing a computer to execute a prescribed program.

A shutdown control process of the X-ray CT apparatus 1 will now be described.

Figure 3:
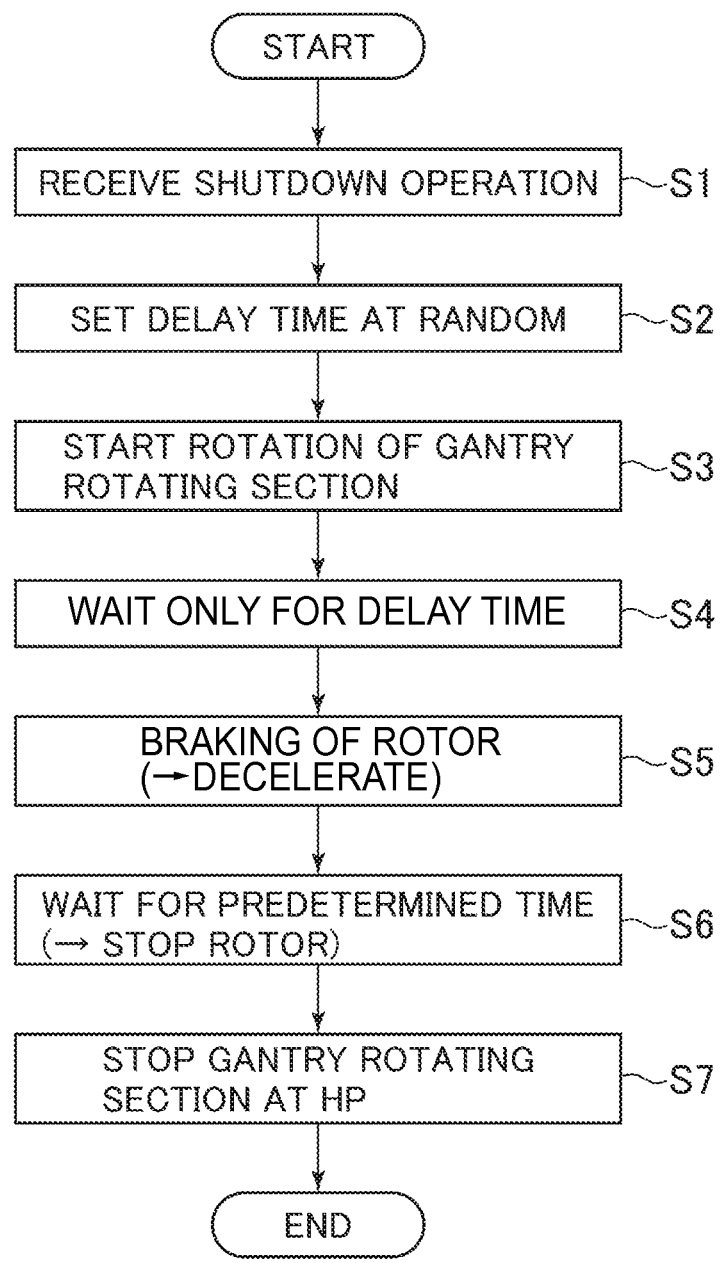
FIG. 3 is a flow diagram depicting the flow of a shutdown control process of the X-ray CT apparatus.
Figure 4:
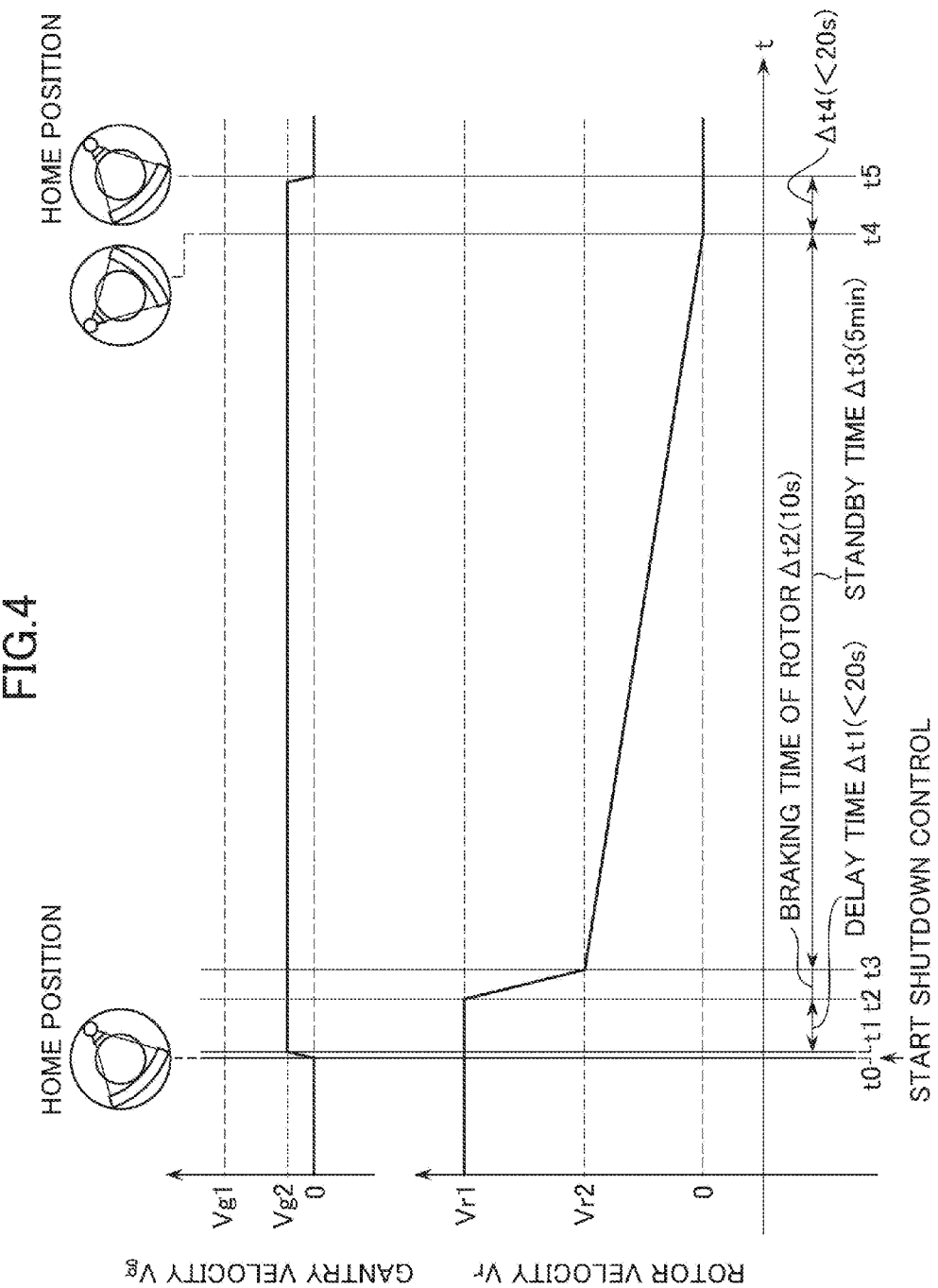
FIG. 4 is a diagram showing one example of temporal changes on the rotation of a gantry rotating section and a rotor in shutdown control of the X-ray CT apparatus.
Figure 5:
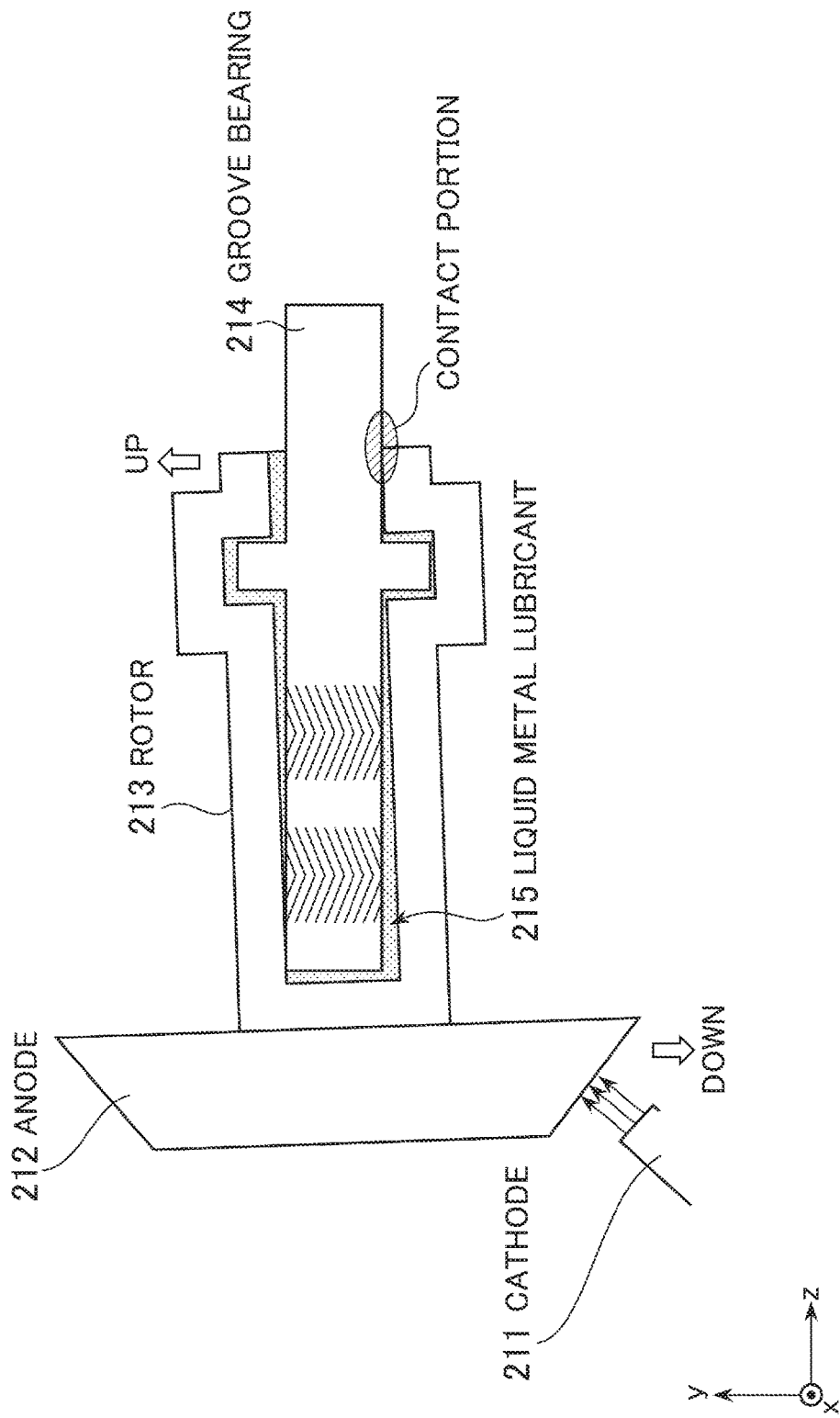
FIG. 5 is a diagram showing the manner in which a rotor of a radiation tube is tiled by its own weight.

FIG. 3 is a flow diagram showing the flow of the shutdown control process of the X-ray CT apparatus 1. Further, FIG. 4 is a diagram showing one example of temporal changes on the rotation of the gantry rotating section 2 and the rotor 213 in the shutdown control of the X-ray CT apparatus 1.

In the present example, first, the gantry rotating section 2 is stopped at the home position HP and the rotor 213 is rotated at a high velocity Vr1.

At step S1, the control unit 6 receives a shutdown operation by an operator. The control unit 6 starts shutdown control at a time t0 when the shutdown operation is received.

At step S2, the control unit 6 sends a control signal to the delay time setting unit 7. The delay time setting unit 7 sets a delay time $\Delta t1$ from the start of the constant-velocity rotation of the gantry rotating section 2 to the start of the control of stop of the rotor 213 at random, based on the control signal. The delay time $\Delta t1$ is set within a time required for the gantry rotating section 2 to rotate one time. In the present example, the delay time $\Delta t1$ is set within 20 seconds. Thus, the rotational angular position of the gantry rotating section 2 at the stop of the rotor 213 is indirectly set at random. It is therefore possible to averagely vary the rotational angular position of the gantry rotating section 2 when the rotor 213 is stopped.

At step S3, the control unit 6 sends a control signal to the gantry driving unit 31. The gantry driving unit 3 starts the rotational driving of the gantry rotating section 2, based on the control signal. The setting of the rotational velocity at this time is done to take a second velocity Vg2 slower than a first velocity Vg1 that is a velocity at the actual scan. The second velocity Vg2 is a velocity that takes 20 seconds per rotation, for example. The gantry rotating section 2 is brought to a constant-velocity rotation at the velocity Vg2 at a time t1 when a slight time has elapsed since the time t0.

At step S4, the control unit 6 waits from the time t1 when the rotation of the gantry rotating section 2 is started at the second velocity Vg2 to a time t2 when the delay time $\Delta t1$ elapses since the time t1.

At step S5, the control unit 6 sends a control signal to the X-ray tube driving unit 22 at the time t2. The X-ray tube driving unit 22 starts the stop control of the rotor 213, based on the control signal. The X-ray tube driving unit 22 applies brakes to the rotor 213 during a predetermined time $\Delta t2$ from the time t2 to t3. The predetermined time $\Delta t2$ is 10 seconds, for example. Thus, the rotor 213 is decelerated from the high velocity Vr1 to the low velocity Vr2.

At step S6, the control unit 6 waits only for a predetermined time $\Delta t3$ from the time t3 to t4. The predetermined time $\Delta t3$ is set as a time required for the rotor 213 to completely stop since it starts its inertial rotation at the velocity Vr2. The predetermined time $\Delta t3$ is 5 minutes, for example. The rotor 213 starts the inertial rotation from the time t3 and is gradually decelerated by the viscous friction force of the liquid metal lubricant 215. Then, the rotor 213 is completely stopped at the time t4.

At step S7, the control unit 6 sends a control signal to the gantry driving unit 31. The gantry driving unit 31 stops the gantry rotating section 2 at the home position HP, based on the control signal. A time $\Delta t4$ from the time t4 when the rotor 213 stops to the time t5 when the gantry rotating section 2 is stopped, is within about 20 seconds.

According to the exemplary embodiment as mentioned above, the rotor 213 of the X-ray tube 21 can be stopped when the gantry rotating section 2 is at the rotational angular position determined at random, while rotating the gantry rotating section 2 at the low velocity when shutting down the X-ray CT apparatus 1. It is thus possible to reduce damage to the groove bearing 214 of the X-ray tube 21 upon stopping of the rotor 213 and vary the location of the damage. It is also possible to suppress a reduction in the service life of the groove bearing 214, i.e., the X-ray tube 2. Further, since the gantry rotating section 2 is no longer stopped during the time from the start of the shutdown control to the time when the gantry rotating section 2 is stopped at the home position to terminate the shutdown control, it is possible to avoid such a dangerous situation that a service engineer starts work during the temporary stop of the gantry rotating section 2 and the gantry rotating section 2 suddenly moves during the work. It is thus possible to shut down the X-ray CT apparatus 1 in safety. Incidentally, when the X-ray CT apparatus 1 is shut down, the stop rotational angular position of the gantry rotating section 2 can be placed in the home position HP. The heat exhaust of the X-ray tube 21 and the heat retention of the X-ray detector 33 can effectively be performed as usual. Further, when the X-ray CT apparatus 1 is started up again, the alignment of a subject 91 can also be performed soon.

Incidentally, in the exemplary embodiment, in order to averagely vary the rotational angular position of the gantry rotating section 2 at the stop of the rotor 213 in the long term, the delay time from the start of rotation of the gantry rotating section 2 at the constant velocity to the start of the stop control of the rotor 213 is set at random. In order to achieve the same purpose, however, for example, the delay time from the start of rotation of the gantry rotating section 2 to the start of the stop control of the rotor 213 is taken to be zero or constant. The rotational velocity of the gantry rotating section 2 may be varied within a prescribed range and set at random. Alternatively, any of a plurality of rotational velocities different from each other may be set sequentially in accordance with a prescribed pattern. Alternatively, both the delay time and the rotational velocity may be set at random, or any of a plurality of combinations different from each other in delay time and rotational velocity may sequentially be set in accordance with a prescribed pattern.

Further, the exemplary embodiment is of the X-ray CT apparatus, but the disclosure is not limited to an apparatus using X-rays and may be an apparatus using gamma rays like other radiation, e.g., a SPECT apparatus.

Many widely different embodiments may be configured without departing from the spirit and the scope of the present invention. It should be understood that the disclosure is not limited to the specific embodiments described in the specification, except as defined in the appended claims.

What is claimed is:

1. A control method of a radiation tomographic imaging apparatus having a gantry rotating section equipped with a radiation tube and a detector, the radiation tube including a liquid bearing and a rotor configured to support an anode and configured to rotate, the method comprising:
   a control step that, when the radiation tomographic imaging apparatus is shut down, is configured to:
      start a rotation of the gantry rotating section at a second velocity slower than a first velocity that is a velocity at an actual scan;
      start control for stopping the rotation of the rotor after a predetermined delay time has elapsed from a starting point of the rotation; and
      control the gantry rotating section and the radiation tube so as to stop the gantry rotating section at a home position after the rotation of the rotor is stopped; and
   a setting step configured to set at least one of the second velocity and the delay time such that a rotational angular position of the gantry rotating section at a time that the rotor stops rotation averagely varies when a shutdown is performed plural times.

2. The control method according to claim 1, wherein in the setting step, the delay time is set at random.

3. The control method according to claim 1, wherein in the setting step, any of a plurality of delay times different from each other is sequentially set in accordance with a prescribed pattern.

4. The control method according to claim 1, wherein the second velocity is a velocity that takes 10 seconds or more per rotation.

5. The control method according to claim 1, wherein the home position is a rotational angular position in which an irradiation direction of a positioning light installed in the gantry rotating section is a predetermined direction.

6. The control method according to claim 1, wherein the home position is a rotational angular position at which the radiation tube approaches a heat exhausting unit.

7. The control method according to claim 1, wherein the home position is a rotational angular position at which the detector approaches a heat retaining unit.

8. A radiation tomographic imaging apparatus having a gantry rotating section equipped with a radiation tube and a detector, the radiation tube including a liquid bearing and a rotor configured to support an anode and configured to rotate, the apparatus comprising:
   a control unit that, when the radiation tomographic imaging apparatus is shut down, is configured to:
      start a rotation of the gantry rotating section at a second velocity slower than a first velocity that is a velocity at an actual scan;
      start control for stopping the rotation of the rotor after a predetermined delay time has elapsed from a starting point of the rotation; and
      control the gantry rotating section and the radiation tube so as to stop the gantry rotating section at a home position after the rotation of the rotor is stopped; and
   a setting unit configured to set at least one of the second velocity and the delay time such that a rotational angular position of the gantry rotating section at a time that the rotor stops rotation averagely varies when a shutdown is performed plural times.

9. The radiation tomographic imaging apparatus according to claim 8, wherein the setting unit is configured to set the delay time at random.

10. The radiation tomographic imaging apparatus according to a claim 9, wherein the home position is a rotational angular position in which an irradiation direction of a positioning light installed in the gantry rotating section is a predetermined direction.

11. The radiation tomographic imaging apparatus according to claim 9, wherein the home position is a rotational angular position at which the radiation tube approaches a heat exhausting unit.

12. The radiation tomographic imaging apparatus according to claim 9, wherein the home position is a rotational angular position at which the detector approaches a heat retaining unit.

13. The radiation tomographic imaging apparatus according to claim 8, wherein the setting unit is configured to sequentially set any of a plurality of delay times different from each other in accordance with a prescribed pattern.

14. The radiation tomographic imaging apparatus according to claim 13, wherein the home position is a rotational angular position in which an irradiation direction of a positioning light installed in the gantry rotating section is a predetermined direction.

15. The radiation tomographic imaging apparatus according to claim 8, wherein the second velocity is a velocity that takes 10 seconds or more per rotation.

16. The radiation tomographic imaging apparatus according to claim 15, wherein the home position is a rotational angular position in which an irradiation direction of a positioning light installed in the gantry rotating section is a predetermined direction.

17. The radiation tomographic imaging apparatus according to claim 8, wherein the home position is a rotational angular position in which an irradiation direction of a positioning light installed in the gantry rotating section is a predetermined direction.

18. The radiation tomographic imaging apparatus according to claim 8, wherein the home position is a rotational angular position at which the radiation tube approaches a heat exhausting unit.

19. The radiation tomographic imaging apparatus according to claim 8, wherein the home position is a rotational angular position at which the detector approaches a heat retaining unit.

20. A program configured to cause a computer to function as the control unit and the setting unit in the radiation tomographic imaging apparatus according to claim 8.

* * * * *